United States Patent [19]
Sher

[11] Patent Number: 6,117,907
[45] Date of Patent: Sep. 12, 2000

[54] TOPICAL TREATMENT OF OCULAR PAIN AFTER CORNEAL SURGERY

[76] Inventor: Neal A. Sher, 2837 Glenhurst Ave. South, Minneapolis, Minn. 55416

[21] Appl. No.: 08/045,761

[22] Filed: Apr. 14, 1993

[51] Int. Cl.[7] ............................................. A61K 31/195
[52] U.S. Cl. ........................................ 514/567; 514/912
[58] Field of Search ................................. 514/567, 912

[56] References Cited

U.S. PATENT DOCUMENTS

| | | | |
|---|---|---|---|
| 4,619,926 | 10/1986 | Eckert | 514/210 |
| 4,665,913 | 5/1987 | L'Esperance, Jr. | 606/5 |
| 4,829,088 | 5/1989 | Doulakas . | |
| 4,960,799 | 10/1990 | Nagy | 514/567 |
| 5,149,693 | 9/1992 | Cagle et al. | 514/40 |

OTHER PUBLICATIONS

Ocular Therapeutics and Pharmacology, Sixth Edition, 1981, pp. 28,258 and 259.
Frucht–Pery, J., et al., "The Effect of Topical Administration of Indomethacin on Symptoms in Corneal Scars and Edema", *American Journal of Opthamology*, 112, 186–190, (Aug. 1991).
"The Effect Of Topical Non Steroidal Anti Inflammatory Drugs (NSAIDS) In Excimer Laser Photorefractive Keratectomy (PRK)" by Steve A. Arshinoff, M.D., ASCRS Symposium, Apr. 15, 1992, San Diego, CA.
N.A. Sher Et Al., Archives Of Ophthalmology, vol. 110, Jul. 1992, pp. 935–943.
"Excimer Lasers In Ophthalmology" by Neal A. Sher, Annual Clao Meeting, Jan. 1992, Las Vegas, NV. Note Attached "Exhibit A".
Agata Et Al., Folia Ophth. Japonica, vol. 35, 1984, pp. 604–612.
A. J. Flach, "Cyclo–oxygenase Inhibitors in Ophthalmology," *Survey of Ophthalmology*, 36, 259–284 (1992).
H. van Husen, Klin. Monatbl. Augenheilk. 188, pp. 615–619 (1986). [English Abstract Provided].
Ophthalmology Times, Oct. 15, 1991, p. 14.
Ophthalmology Times, Mar. 15, 1993, pp. 26–28.
Araie et al., Jpn. J. Ophthalmol. 27, pp. 535–542 (1983).
Ocular Surgery News, Mar. 15, 1993, p. 64.
Ocular Surgery News, May 1, 1992, pp. 24–25.
Monatsbl. Augenheilk. 200, 362–366 (1992). [English Abstract Only].
Physicians Desk Reference For Ophthalmology, 20 Edition, pp. 268–269 (1992).
"Flurbiprofen–An Ophthalmic NSAID", *The Medical Letter on Drugs and Therapeutics*, 29, 59 (1987).
Skoutakis et al., "Review of Diclofenac and Evaluation of its Place in Therapy as a Nonsteroidal Antiinflammatory Agent", *Drug Intell.& Clin. Pharm.*, 22, 850 (1988).
Podos et al., "Comparison of ocular prostaglandin synthesis inhibitors", *Investig. Opthal.*, 15, 841 (1976).
Rooks et al., "The Analgesic and Anti–Inflammatory Profile of Ketorolac and its Tromethamine Salts", *Drugs Exptl. Clin. Res.*, XI(8), 479 (1985).
Todd et al., "Suprofen: A Review of its Pharmacodynamic and Phamracokinetic Properties, and Analgesic Efficacy", *Drugs*, 30, 514 (1985).
Kantor, "Use of Diclofenac in Analgesia", *Amer. J. Med.*, 80, 64 (1986).

*Primary Examiner*—Zohreh Fay
*Attorney, Agent, or Firm*—Schwegman, Lundberg, Woessner & Kluth, P.A.

[57] ABSTRACT

Post-operative method for the treatment of ocular pain following corneal reprofiling surgery by topical administration of an ophthalmic nonsteroidal solution and an ophthalmic steroidal composition. The nonsteroidal solution comprises a non-steroidal anti-inflammatory agent such as diclofenac sodium and the steroidal composition contains a corticosteroid such as fluorometholone. These ophthalmic medicaments when used in combination reduce the post-operative pain particularly associated with phototherapeutic keratectomy and photorefractive keratectomy performed with an excimer laser and promote re-epithelialization over the reprofiled corneal surface.

4 Claims, No Drawings

TOPICAL TREATMENT OF OCULAR PAIN AFTER CORNEAL SURGERY

BACKGROUND OF THE INVENTION (1). Field of the Invention

This invention relates to a method for the topical treatment of ocular pain following corneal surgery. More particularly, the invention relates to the topical ophthalmic use of a non-steroidal anti-inflammatory agent in combination with a steroid for treating post-operative pain associated with corneal reprofiling surgeries.

(2). Description of the Prior Art

Various surgical procedures are known for altering the geometry of the cornea to correct refractive errors in vision. Such surgical procedures include radial keratotomy (RK) which is intended to correct myopia caused by excessive corneal curvature. In this procedure, a series of incisions is made in the cornea, usually penetrating about 90 to 95% of the thickness of the cornea. The incisions radiate outwardly from the corneal center and allow the cornea to relax and to flatten out somewhat, thereby reducing or eliminating nearsightedness. Similar corneal reprofiling procedures such as incisional keratotomy (IK), in which the incisions are made in directions other than radial, have been employed to correct certain astigmatisms.

Until recently, such surgical procedures were commonly carried out using instruments such as diamond or steel knives and razors. However, the results achieved in corneal operations using mechanical instruments are not highly predictable or controllable in any given patient and some patients have encountered post-operative discomfort and moderate pain related to damaged ocular tissue caused by surgical abrasion.

Recently, new laser surgical techniques have been developed which ablate the cornea to alter its refractive properties or otherwise treat corneal abnormalities. These laser reprofiling techniques include phototherapeutic keratectomy (PTK) in which laser radiation is applied to the cornea with minimal heating effects to ablate or smooth the cornea and remove opacities. When used to ablate very thin layers of corneal tissue to alter the curvature of the cornea for reducing or eliminating myopia, hyperopia or astigmatism, the procedure is typically referred to as photorefractive keratectomy (PRK). These corneal reshaping operations are presently performed with a high energy excimer laser which emits ultraviolet (UV) radiation capable of removing corneal tissue in a precise and incremental manner without thermal damage to surrounding tissue. For further details on PRK techniques, reference is made to Marshall et al., "Photoablative Reprofiling Of The Cornea Using An Excimer Laser: Photorefractive Keratectomy," Lasers in Ophthalmology, Vol. 1, pp. 21–48 (1986). Also, U.S. Pat. No. 4,665,913 to L'Esperance describes a PRK procedure for changing the contour of the anterior surface of the cornea by directing pulses from an excimer laser in a scanning pattern that moves around the cornea.

In clinical trials of PTK and PRK procedures, patients typically experience significant ocular pain immediately following surgery, which usually persists until corneal re-epithelialization. Despite the post-operative use of cold compresses, bandage soft contact lenses, cycloplegics, narcotics and corticosteroidal ophthalmic agents, patients usually describe the pain as severe, sometimes throbbing in nature and associate it with a burning, stinging sensation, as well as photophobia, tearing and nasal congestion. Some patients have characterized this type of pain as the worst they have ever experienced.

A number of ophthalmic substances have been reported in the patent literature for the control or treatment of ocular inflammation. For instance, U.S. Pat. No. 4,829,088 to Doulakas describes a ophthalmic medicament containing diclofenac sodium in aqueous solution for the treatment of inflammation of the eye. Also, U.S. Pat. No. 4,960,799 to Nagy (assigned to Ciba-Geigy Corp.) discloses that diclofenac sodium in the form of an aqueous solution can be useful in the control of post-operative inflammation resulting from cataract removal. However, the patentee fails to mention post-operative pain. This may be due to the fact that the severity of pain associated with complex corneal surgeries of the type described hereinabove is not commensurate with the relatively moderate discomfort associated with cataract removal. Moreover, these prior art formulations when used alone were found to be less effective in treating ocular pain of the type associated with such corneal surgeries.

Hence, there exists a need for a post-operative method for treating the newly reprofiled surface of the cornea to attenuate the pain, burning, stinging, photophobia and other adverse sensations that often accompany corneal surgical procedures.

SUMMARY OF THE INVENTION

Accordingly, it is an object of the present invention to provide a method for the immediate treatment or control of post-operative pain of the type associated with surgical procedures on the cornea of the eye.

It is a further object of the invention to provide a safe and effective post-operative procedure for treating severe pain and other adverse sensations following excimer laser photorefractive keratectomy (PRK), phototherapeutic keratectomy (PTK), radial keratotomy (RK) and incisional keratotomy (IK).

These and other objects are accomplished in accordance with the present invention which provides a method of treating post-operative ocular pain following corneal surgery which comprises administering topically to the effected eye of a human host a therapeutically effective amount of an aqueous ophthalmic solution of a nonsteroidal anti-inflammatory drug, and an ophthalmic composition comprising a corticosteroid in a pharmaceutical acceptable carrier therefor.

In a preferred embodiment of the invention, the present method can be safely used to substantially reduce the post-operative pain and suffering experienced by patients who have undergone excimer PRK and PTK. Thus, the method of the present invention would eliminate a significant problem associated with this surgical technique, which continues to generate wide interest for the treatment of refractive errors and corneal scars, and offers readily apparent advantages over the inconveniences afforded by conventional methods of vision correction, i.e., corrective lenses such as eyeglasses or contact lenses.

The foregoing and other aspects, advantages and objects of the invention may be more fully appreciated by reference to the following detailed description.

DETAILED DESCRIPTION OF THE PREFERRED EMBODIMENTS

As noted above, it has been found that the immediate post-operative use of an ophthalmic nonsteroidal anti-inflammatory drug (NSAID) solution combined with a topical corticosteroid significantly reduces the pain after corneal surgery, especially following excimer PRK and PTK.

The NSAID solution utilized in the method of the present invention can be any such formulation suitable for topical use. The topical NSAID solutions should preferably be isotonic and have a relatively neutral pH. Conventionally, ophthalmic solutions are rendered isotonic by the addition of alkali metal salts, preferably sodium salts. Representative of such ophthalmic formulations include aqueous solutions of diclofenac, flubriprofen, suprofen and ketorolac. Other equivalent ophthalmic formulations may also be selected. In this regard, attention should be focussed on the formulation's ability to reduce post-operative ophthalmic pain synergistically in combination with a topical corticosteroid. One such synergistic pain reducing combination would be the blocking of separate intermediate pathways involved in the production of pain-producing prostaglandins.

A particularly preferred ophthalmic NSAID formulation for use in the present method is a 0.1% aqueous solution of diclofenac sodium, available from Ciba Vision Ophthalmics, Atlanta, Ga., under the trademark VOLTARIN OPHTHALMIC. Diclofenac sodium itself is designated chemically as 2-[(2,6-dichlorophenyl)amino] benzoacetic acid, monosodium salt, with an empirical formula $C_{14}H_{10}Cl_2NO_2Na$ and is a potent aniline phenylacetate nonsteroidal anti-inflammatory drug conventionally used in relieving the signs and symptoms associated with rheumatoid arthritis, degenerative joint disease and allied conditions. Diclofenac sodium belongs in a class of drugs which are known as cyclo-oxygenase inhibitors (COIs) which includes flubiprofen (OCUFEN, Allergan Co.), Suprofen (PROFENAL, Alcon), and most recently ketorolac (ACULAR, Allergan).

In 1991, VOLTAREN OPHTHALMIC was introduced in the U.S. for the treatment of postoperative inflammation following cataract surgery. For a detailed description of this marketed formulation, reference is made to aforementioned U.S. Pat. No. 4,960,799.

Various topical ophthalmic compositions comprising a corticosteroid in an acceptable carrier would be suitable in the present method. Examples of suitable corticosteroids include prednisolone acetate, fluorometholone or its acetate, dexamethasone, and hydrocortisone acetate. Again, other equivalent ophthalmic corticosteroid compositions may be selected. Compositions of these particular steroids can be administered as solutions, suspensions, or dispersions in a suitable ophthalmic vehicle.

A particularly preferred corticosteroidal composition for use in the present method is a 0.1% fluorometholone solution. Fluorometholone itself is a corticosteroid described as 21-desoxy-9a-fluoro-6a methylprednisolone, and was traditionally used topically in the treatment of allergic dermatoses and other inflammatory skin conditions.

The frequency and duration of topical administration of the foregoing ophthalmic NSAID solution and corticosteroidal composition, the sequence of administration, and concentration of treatment agents may obviously vary depending upon a number of factors, including the nature of the corneal surgical procedure, the extent of corneal reprofiling, the medical history of the patient, symptoms prior to, during or after surgery, and the extent of the refractive condition of the eye. Selection of a particular treatment agent or its concentration can be made by the skilled clinician guided by the foregoing description.

The method of the present invention may be practiced in conjunction with the post-operative use of cold compresses, bandage soft contact lenses, antibiotics, cycloplegics, narcotics and other ophthalmic agents. For instance, the broad spectrum aminoglycoside antibiotic tobramycin and the parasympathetic cycloplegic homatropine hydrobromide, $C_{16}H_{21}NO_3HBr$, in suitable ophthalmic vehicles may additionally be topically administered immediately following ablation. Also, during the present post-operative treatment, the patient may be permitted to use aspirin, acetaminophen, Mepergan Fortis (50 mg of meperidine and 25 mg of promethazine) (Wyeth-Ayerest, Philadelphia, Pa.) and oral narcotics as needed. In view of the present disclosure, the specific regimen used in administering these and other ocular treatment agents in combination with the method of the present invention would be well within the purview of any person skilled in the art.

In addition, a disposable bandage soft contact lens may be placed atop the treated eye following corneal surgery to foster re-epithelialization. As an alternative to the bandage soft contact lens, collagen shields or patching may also be used in conjunction with the present method to enhance re-epithelialization.

Rapid epithelialization after corneal surgery is desirable for a number of reasons including the elimination of pain and discomfort, the reduced risk of infection and the more rapid improvement of visual acuity. While it is not known which combination of postoperative regimens will aid in achieving the quickest re-epithelialization, further clinical study is underway to refine this determination. It is known that the use of a bandage soft contact lens may predispose the eye to a higher risk of bacterial keratitis and delayed healing in some patients. This risk may be offset by the more frequent application and higher concentration of antibiotics. However, it is believed that the immediate use of a bandage soft contact lens improves patient comfort and promotes an earlier return of visual acuity.

In a specific embodiment of the inventive method, a patient is topically administered an ophthalmic aqueous solution of diclofenac sodium immediately after myopic PRK. The patient is also post-operatively administered fluorometholone 0.1% solution. Tobramycin 0.3% ophthalmic solution and 5% homatropine hydrobromide are also administered post-operatively as an antibiotic and a cycloplegic, respectively. The patient is then fitted with a disposable soft contact lens. Subsequent to this initial administration, the topical diclofenac sodium regimen is repeated four times a day.

In this specific embodiment, the diclofenac sodium ophthalmic aqueous solution contains diclofenac sodium at a 1 mg/mL concentration. Further, the aqueous solution comprises boric acid, disodium ethylenediamine tetraacetic acid (1 mg/mL), polyoxyl (35 mol.) castor oil, purified water, sorbic acid (2 mg/mL), and tromethamine. The solution is contained in a sterile plastic dropper bottle adapted for ocular administration.

More specifically, immediately after the laser procedure, the patient is administered one drop of the diclofenac sodium ophthalmic solution. Immediately following the ablation, 0.1% fluorometholone is started and followed every two hours. Additionally, the 0.3% tobramycin drops is given four times daily and the 5% homatropine hydrobromide is administered immediately postoperatively. The disposable soft contact lens having a +0.50 diopter is placed over the ablated zone. The diclofenac sodium solution was subsequently applied to the operative eye every six hours.

The specific embodiment set forth hereinabove has been clinically studied to determine its effectiveness. The following clinical study is representative of results obtained by the method of the present invention.

Clinical Study

A randomized, double-masked parallel group study of diclofenac sodium 0.1% ophthalmic solution (DSO) or its placebo vehicle (PLA) was performed in accordance with the specific embodiment of the present invention. Patients undergoing excimer myopic PRK on their second eye were admitted overnight. Postoperative procedures included two drops of DSO or PLA immediately after surgery and then four times a day, topical tobramycin (q.i.d), 0.1% fluorometholone (q. 2 h.), cycloplegics, and a disposable soft contact lens. Thirty two patients (DSO=16, PLA=16) were evaluated from 30 minutes to +96 hours by several types of questionnaires. Patients that received placebo experienced pain, starting at one hour, peaking at 4 hours and lasting 36–48 hours. The DSO-treated patients rarely experienced the early peak in pain and had less pain until 36 hours post-op and experienced significantly less photophobia, burning and stinging. Significantly fewer patients on DSO required oral narcotics. Three patients (DSO=2, PLA=1) developed corneal infiltrates, the etiology of which is not known. The following tables summarize the results of the clinical study:

Legend to Tables

Table 1: Summary of total pain in the first 6 and first 24 hours and the maximum pain intensity during the first 24 hours.

Table 1a: Samples of categorical pain scale.

Table 1b: Visual Analog Scale.

Table 1c: Ocular descriptions.

All filled out by the patients.

Table 2: Ocular Pain Assessment at 24 hours after Excimer PRK. Represents summary of Categorical Scale. Represents means of 16 patients in Placebo group and 16 patients in Diclofenac group.

Table 3: Patient Assessment of Pain, Categorical Scale. Time course of pain to 96 hours after surgery. All points represent mean of 16 patients in each group. Extended bars represent S.E.

Table 4: Patient Assessment of Pain, Visual Analog Scale. Represents time course of pain to 96 hours. All points represent mean of 16 patients in each group. Extended bars represent S.E.

Table 5: Patient Assessment of Light Sensitivity after PRK. Represents time course to 96 hours after surgery. All points represent mean of 16 patients in each group. Extended bars represent S.E.

Table 6: Patient Assessment of Stinging and Burning after PRK. Represents time course to 96 hours after PRK. All points represent the mean of 16 patients in each group. Extended bars represent S.E.

Table 7: Percent of Patients Taking 0, 1, 2, 3 or 4 Oral Narcotic Pills During the First 24 Hours After Excimer PRK.

TABLE 1

| Efficacy Variable | P-Value* Categorical Scale | Visual Analog Scale |
|---|---|---|
| Total pain intensity first 6 hours | <0.01 | <0.01 |
| Total pain intensity first 24 hours | <0.01 | <0.01 |
| Maximum pain intensity first 24 hours | <0.001 | <0.05 |

*Statistically significant difference between DSO and PLA (two-sided) by the Wilcoxin rank sum test. In all cases, the DSO group was favored.

TABLE 1a

CATAGORICAL PAIN SCALE - COMPLETED BY PATIENT a. The amount of pain in your eye at this moment is:

| | NONE | MILD | MODERATE | SEVERE |
|---|---|---|---|---|
| Operated Eye | 0 | 1 | 2 | 3 |
| Opposite Eye | 0 | 1 | 2 | 3 |

TABLE 1b

VISUAL ANALOG PAIN SCALE - COMPLETED BY PATIENT b. Please place an "X" on the dark, solid line below to indicate the amount of pain, if any, that you feel at this moment in your operated eye:

```
           Mild         Moderate        Severe
         |------|      |--------|     |-------|
No       |-------------------------------------|  Worst
Pain                                             Pain
                                                 Ever
```

TABLE 1c

OCULAR DESCRIPTORS - COMPLETED BY PATIENT c. In each category, circle one term which describes the type of sensation that you feel at this moment in your operated eye:

| | NONE | MILD | MODERATE | SEVERE |
|---|---|---|---|---|
| Foreign Body Sensation | 0 | 1 | 2 | 3 |
| Light Sensitivity | 0 | 1 | 2 | 3 |
| Deep Headache-Like Pain Within Eye | 0 | 1 | 2 | 3 |
| Stinging/Burning | 0 | 1 | 2 | 3 |
| Itching | 0 | 1 | 2 | 3 |

Temperature   0. HOT   1. WARM   2. NORMAL   3. COOL   4. COLD

TABLE 2
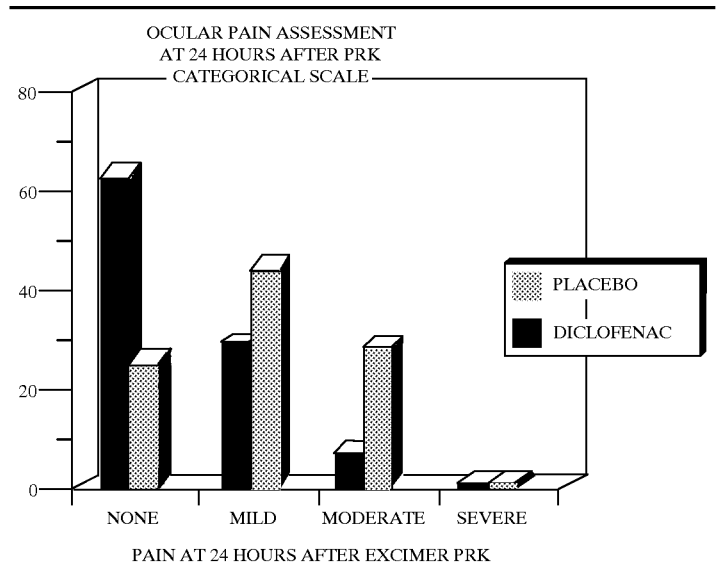
TABLE 3
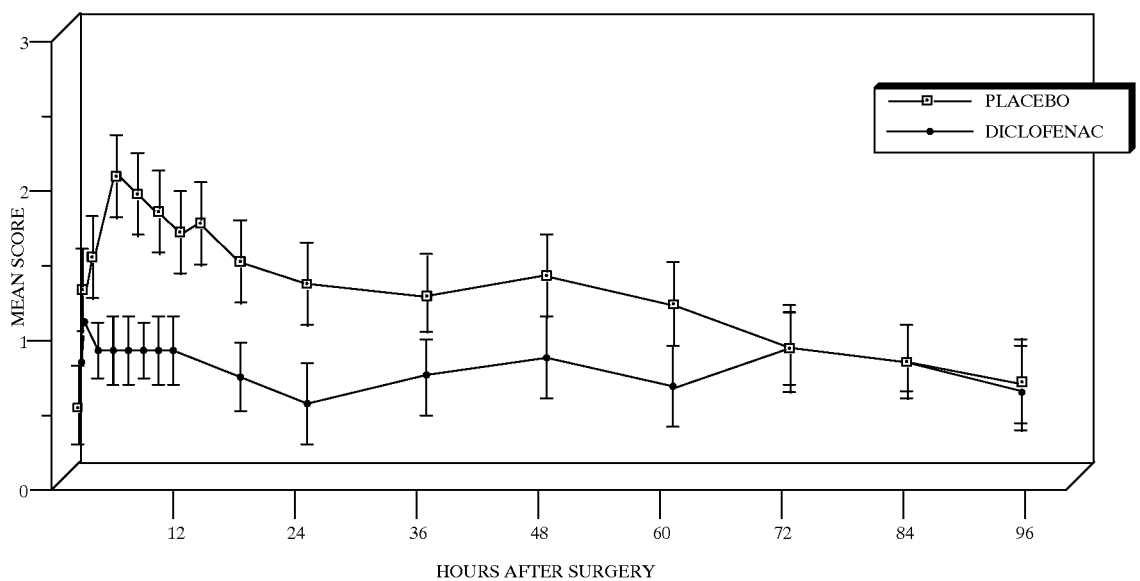

TABLE 4
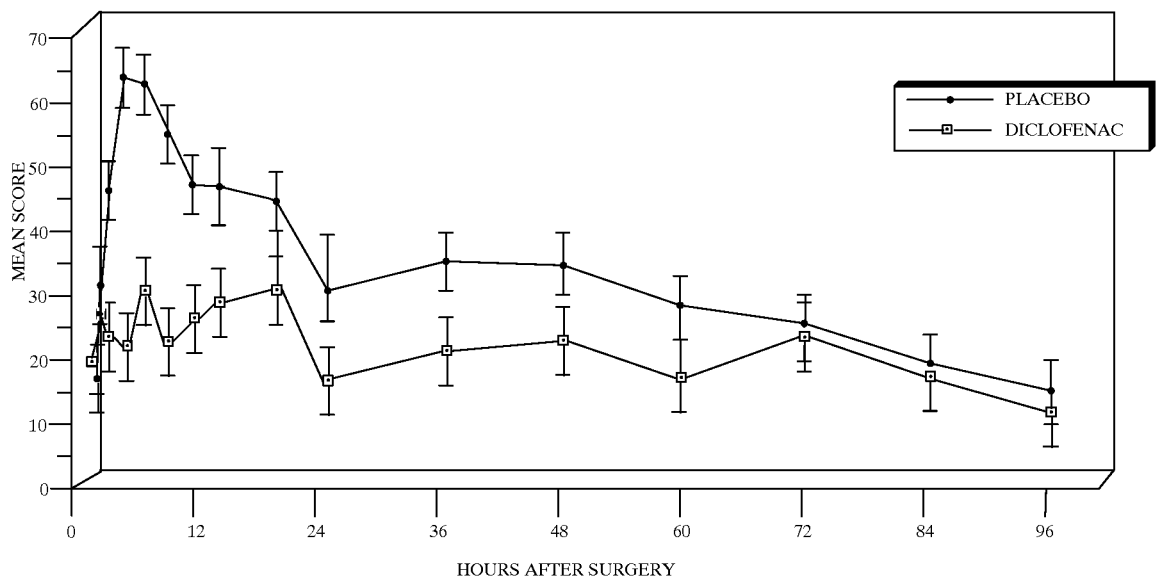
PATIENT ASSESSMENT OF PAIN
VISUAL ANALOG SCALE
TABLE 5
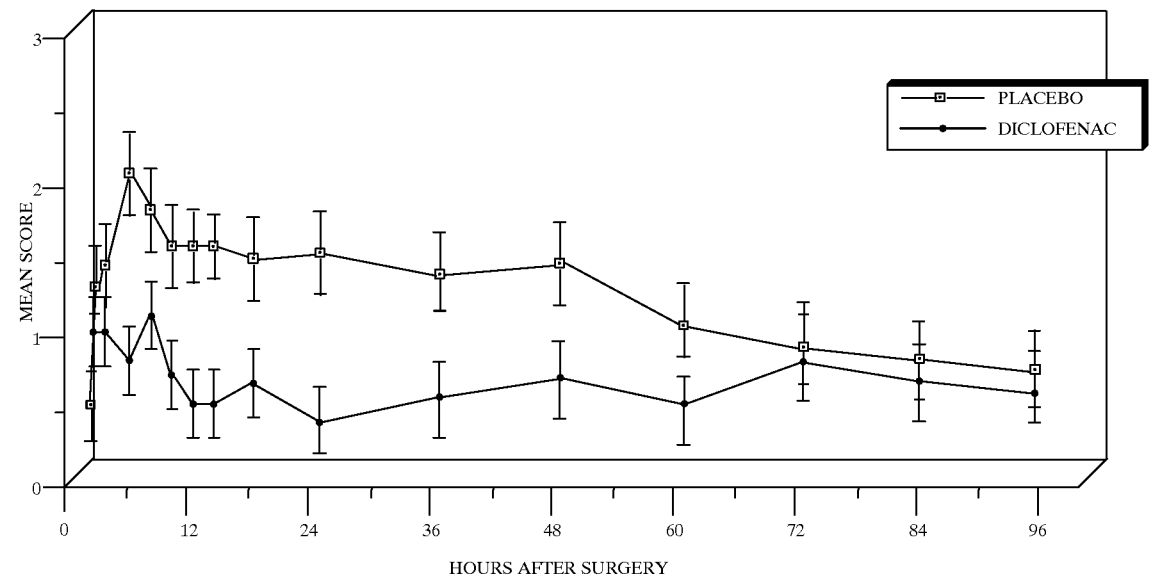
PATIENT ASSESSMENT OF LIGHT SENSITIVITY
96 HOURS AFTER PRK

TABLE 6

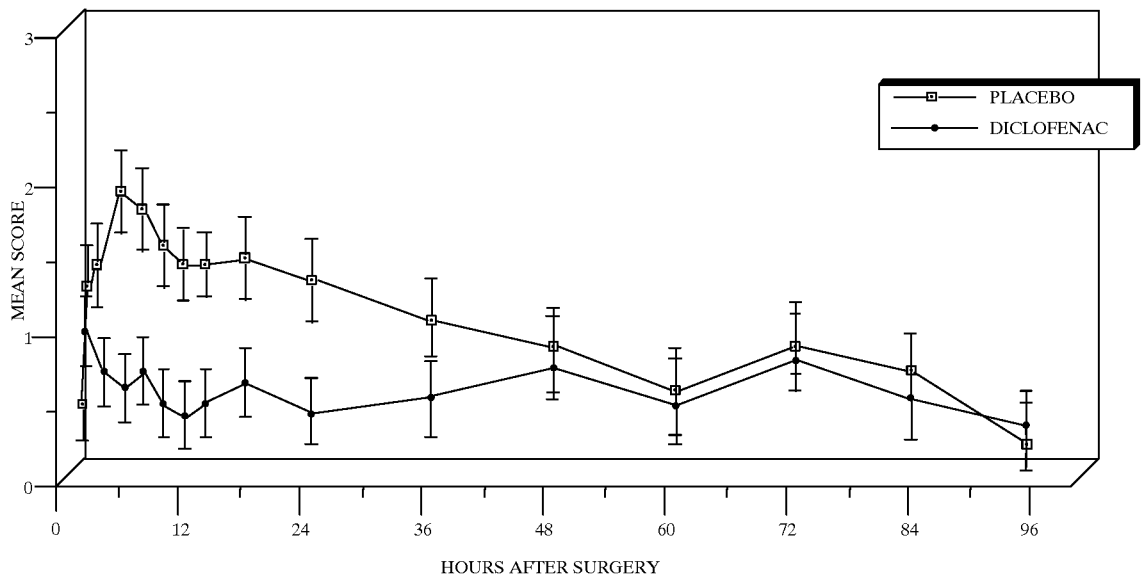

TABLE 7

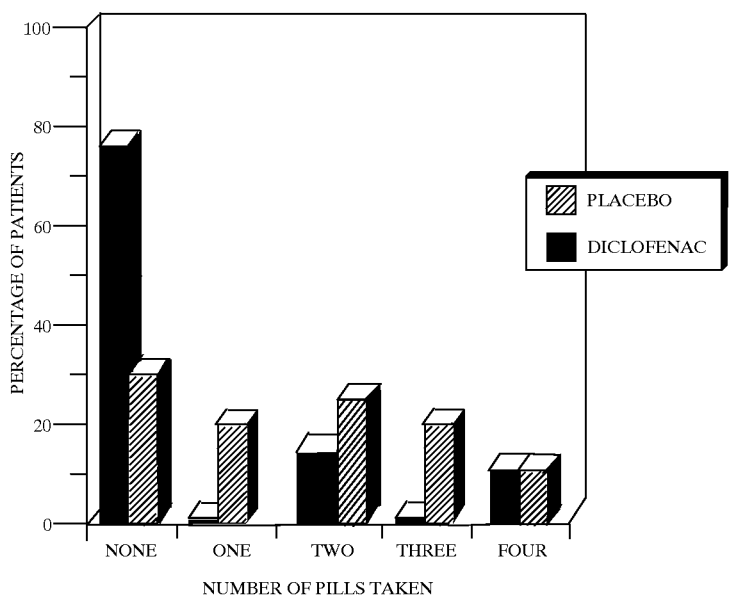

As shown in the tables, the unexpected results of the study are clearly demonstrative of the post-operative use of DSO and topical fluorometholone in significantly reducing pain after excimer PRK. It is believed that such results will revitalize interest in pioneer PRK technology, a technology where problems associated with post-operative pain have been long felt, and until now, unsolved.

The specific mechanisms underlying the post-PRK/PTK pain-relieving effect of diclofenac sodium as a component in the specific embodiment of the invention is presently unknown, but is believed to be dependent on several factors. It has been advanced that, as a COI, its effects may be mediated through the effect on the cyclo-oxygenase pathway. COIs display an anti-inflammatory effect which in some instances results by inhibiting the production of prostaglandins, and more specifically, by blocking the transformation of arachidonic acid (AA) to pain-producing prostaglandins.

As with the diclofenac sodium ophthalmic solution, the specific mechanisms underlying the post-PRK pain reducing effect of fluorometholone in the specific embodiment may also be dependent on several factors. It is advanced that like diclofenac sodium, fluorometholone inhibit prostaglandin biosynthesis. However, fluorometholone acts at an earlier location in the pathway by reducing levels of phospholipase $A_2$ which normally aids in the production of AA from the phospholipase pool. It is believed that the combined use of fluorometholone and diclofenac sodium to block separate intermediate pathways results in the unique synergistic post-PRK pain-reducing effect accomplished by the present method.

It should be understood that the suggested interpretation by which the present therapeutic method operates to produce the post-operative analgesic results is merely proposed as a theoretical guide. It is not intended that the present invention be limited to any particular theory or mechanism involving interrelated biological systems.

It should be further understood that there may be various changes and modifications of the representative embodiments herein chosen for purposes of description without departing from the spirit and scope of the invention. Accordingly, the foregoing descriptions are not to be interpreted as restrictive of the invention beyond that necessitated by the following claims.

I claim:

1. A method of treating post-operative ocular pain following corneal laser reprofiling surgery which comprises administering topically to the effected eye of a human host immediately after said laser reprofiling surgery a therapeutically effective amount of an aqueous opthalmic solution of diclofenac or isotonic salts thereof which is effective to reduce the noninflammation-associated ocular pain.

2. The method according to claim 1 wherein said corneal laser reprofiling surgery is selected from the group consisting of photorefractive keratectomy and phototherapeutic keratectomy.

3. The method according to claim 2 wherein said corneal laser reprofiling surgery is photorefractive keratectomy performed with a high energy excimer laser.

4. The method according to claim 1 wherein the effected eye is covered with a bandage soft contact lens.

* * * * *

UNITED STATES PATENT AND TRADEMARK OFFICE
CERTIFICATE OF CORRECTION

PATENT NO.: 6,117,907

DATED: Sep. 12, 2000

INVENTOR(S) : Sher

It is certified that error appears in the above-identified patent and that said Letters Patent is hereby corrected as shown below:

In column 3, line 43, delete "9a-fluoro-6a" and insert --9α-fluoro-6α--, therefor.

Signed and Sealed this

First Day of May, 2001

*Attest:*

NICHOLAS P. GODICI

*Attesting Officer*     Acting Director of the United States Patent and Trademark Office